United States Patent [19]

Stringer et al.

[11] Patent Number: 4,593,106
[45] Date of Patent: Jun. 3, 1986

[54] 4-[2-(DIALKYLAMINO)ETHYL]-7-HYDROXYISATINS

[75] Inventors: Orum D. Stringer, Philadelphia; Joseph Weinstock, Phoenixville; James W. Wilson, Wayne, all of Pa.

[73] Assignee: SmithKline Beckman Corporation, Philadelphia, Pa.

[21] Appl. No.: 616,635

[22] Filed: Jun. 4, 1984

[51] Int. Cl.$^4$ ............................................ C07D 209/38
[52] U.S. Cl. ..................................... 548/485; 514/418
[58] Field of Search ......................... 548/485; 514/418

[56] References Cited

U.S. PATENT DOCUMENTS

| | | | |
|---|---|---|---|
| 4,314,944 | 2/1982 | Huffman et al. | 424/274 |
| 4,395,559 | 7/1983 | Fothergill | 548/485 |
| 4,414,224 | 11/1983 | Huffman | 514/418 |

*Primary Examiner*—Donald G. Daus
*Assistant Examiner*—Robert Benson
*Attorney, Agent, or Firm*—Joseph A. Marlino; Stuart R. Suter; Alan D. Lourie

[57] ABSTRACT

4-[2-(Dialkylamino)ethyl]-7-hydroxyisatins are prepared by internal condensation of an oxime followed by removal of protecting groups. The compounds are $D_2$-agonists and, thereby, have anti-hypertensive activity. A species of the group is 4-[2-(di-n-propylamino)ethyl]-4-hydroxyisatin.

2 Claims, No Drawings

4-[2-(DIALKYLAMINO)ETHYL]-7-HYDROXYISATINS

This invention relates to new chemical compounds which are 4-[2-(dialkylamino)ethyl]-7-hydroxyisatins. The claimed pharmaceutical compositions and methods which use these compounds as active ingredients relate to inducing dopaminergic or $D_2$-agonist activity useful for treating hypertension.

DESCRIPTION OF THE PRIOR ART

U.S. Pat. No. 4,314,944 discloses a series of 4-aminoalkyl-7-hydroxy-2(3H)-indolones which have renal dopaminergic activity. An isatin intermediate is described in the reaction sequence for preparing these indolones. No biological activity is mentioned for the isatin compound. Nor can those intermediates be used readily to prepare the compounds of this invention due to the chemically reactive 2,3-diketo system of the hereafter described anti-hypertensive isatins.

DESCRIPTION OF THE INVENTION

The compounds of this invention are illustrated by the following structural formula:

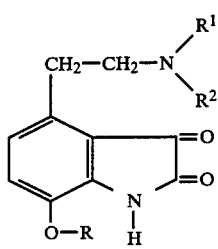

in which:
R is hydrogen or methyl, and
$R^1$ and $R^2$ are, each, $C_{1-6}$-alkyl, benzyl, phenethyl, methoxyphenethyl or hydroxyphenethyl.

The compounds of formula I in which $R^1$ and $R^2$ are both n-propyl or are n-propyl, 4-hydroxyphenethyl, with R being hydrogen in each instance, are preferred.

The pharmaceutically acceptable acid addition salts which have the utility of the free bases of formula I are part of this invention. These are prepared by methods well known to the art and are formed with both nontoxic inorganic or organic acids, for example: maleic, fumaric, benzoic, ascorbic, pamoic, succinic, bismethylenesalicylic, methane sulfonic, ethane disulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric or nitric acids. The hydrohalic and, especially, methane sulfonic acid salts are conveniently used.

Also included in this invention are the O—$C_{2-6}$-alkanoyl derivatives of the compounds of formula I. These are prepared by O-acylation of compounds of formula I, preferably as a salt, with a lower alkanoyl halide or anhydride in the presence of a base.

The compounds of formula I are prepared by the following reaction sequence:

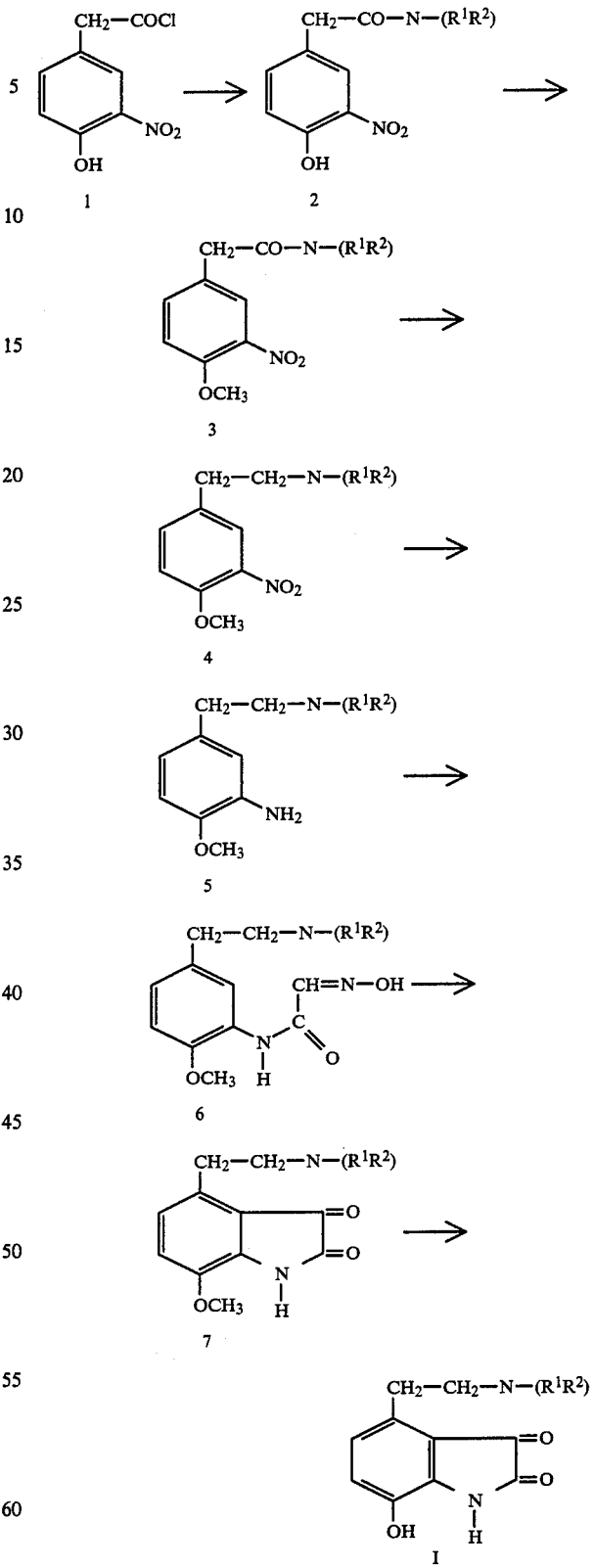

in which $R^1$ and $R^2$ are as defined above.

In the above reaction sequence, suitable secondary amines, with any chemically sensitive centers protected, are reacted with the substituted phenacetyl halide, 1. For example, a hydroxy group may be in the form of a methyl or benzyl ether with optional removal at the last dealkylation step if not before.

The 3-amino-4-methoxyphenethylamine, 5, is a key intermediate in the reaction sequence. This compound is reacted with chloral hydrate and hydroxyl amine sulfate in dilute acid medium at reflux temperature to give the oxime, 6, which is, then, cyclized by heating it in sulfuric acid to give the 4-aminoethyl-7-methoxyisatin.

The final step of the sequence involves the dealkylation of the O-protected products of structure 7. Optional dealkylation at position 7 as well as at any other protected groups such as the 4'-alkoxy substituent on the aromatic ring (when $R_1$ or $R_2$=phenethyl) is accomplished by the reaction of intermediate 7 with refluxing 48% hydrogen bromide, boron tribromide or boron trichloride in the cold, hydriodic acid, aluminum chloride, pyridine hydrochloride or other dealkylation-splitting agents. The temperature range can vary from $-15°$ to reflux temperatures depending on the nature of the protecting groups and the dealkylating agent as known to the art. The reaction is usually complete in from 1-5 hours. The desired product is isolated as the base or as an acid addition salt by conventional chemical methods.

The overall reaction sequence is illustrated in Example 1 hereafter.

The compounds of this invention have utility, as specific dopamine agonists, in the treatment of disorders of the cardiovascular system, especially to treat hypertension, to treat angina pectoris, to treat the symptoms of congestive heart failure or to improve kidney function.

More specifically, the compounds of this invention, especially 4-[2-(N,N-di-n-propylamino)ethyl]-7-hydroxyisatin hydrobromide, have proved to be selective peripheral $D_2$-agonists. Otherwise speaking, the main locus of action is at the presynaptic dopaminergic receptors or sympathetic nerve terminals which may also be called "$D_2$-receptors." Activation of the $D_2$-receptors on the sympathetic nerve terminals inhibits the release of norepinephrine, thereby, inhibiting the increases in cardiac rate and the peripheral vasoconstriction resulting from stimulation of the sympathetic nervous system. These are beneficial cardiovascular actions in those conditions involving excessive or inappropriate levels of sympathetic nervous system stimulation.

In the perfused rabbit ear artery test for $D_2$-agonist activity, the above-named compound had an $EC_{50}$ in the range of from 2-7 nM. In the same test system, N,N-di-n-propyldopamine had an $EC_{50}$ of from 50-60 nM.

The pharmaceutical compositions of this invention, which have pharmacodynamic activity within the cardiovascular system, for example renal vasodilatation, the ability to correct hemodynamic imbalance, antianginal activity, anti-hypertensive activity and bradycardia, are prepared in conventional dosage unit forms by incorporating a compound of formula I, or a pharmaceutically acceptable acid addition salt or ester thereof, into a nontoxic pharmaceutical carrier according to accepted pharmacy procedures in a nontoxic quantity sufficient to produce the desired pharmacodynamic activity in an animal or human patient. Preferably, the compositions will contain the active ingredient in an active but nontoxic quantity which is selected from the range of about 10 mg to about 300 mg, preferably about 50-150 mg of active ingredient, as the base, per dosage unit. This quantity depends on the relative potency of the base compound compared with that of the prototypic species, 4-[2-(N,N-di-n-propylamino)ethyl]-7-hydroxyisatin, as well as on the specific biological activity desired, the route of administration, that is, whether oral or parenteral, and the condition and size of the patient.

The pharmaceutical carrier employed for the dosage units is, for example, either a solid or liquid. Exemplary of solid carriers are lactose, terra alba, sucrose, talc, gelatin, agar, pectin, acacia, magnesium stearate or stearic acid. Exemplary of liquid carriers are isotonic saline for parenteral use or syrup, peanut oil, olive oil or water for soft gelatin capsules. Similarly, the carrier or diluent may include any time delay material well known to the art, such as cellulose esters or ethers and glycerol esters alone or admixed with a wax. Such sustained release products as well as prodrug derivatives which may be gradually metabolized to the active parent can be employed to prolong the unique biological activity of the compounds of this invention or to attack receptors at a specific location.

A wide variety of pharmaceutical forms can be employed. Thus, if a solid carrier for oral or rectal administration is used, the mixed preparation can be tableted, placed in a hard gelatin capsule in powder or sustained release pellet form, dermal patch, in a suppository or in the form of a troche or lozenge. The amount of solid carrier will vary widely but, preferably, will be from about 25 mg to about 1 g. If a liquid carrier is used, the preparation will be in the form of a syrup, emulsion, soft gelatin capsule, sterile injectable liquid for an ampul or multidose vial, or an aqueous or nonaqueous liquid suspension for oral administration.

Advantageously, doses selected from the dosage unit ranges given above will be administered several times, such as from one to five times, a day. The daily dosage regimen is selected from the range of about 10 mg to about 1.0 g, preferably 50-500 mg for oral administration and 10-250 mg for parenteral administration. When the method described above is carried out, $D_2$-agonist activity is produced.

Using 4-[2-(di-n-propylamino)ethyl]-7-hydroxyisatin hydrobromide as an active ingredient, a nontoxic, $D_2$-agonist dose, for an average size human, would be selected from the range of from about 25-150 mg of base for each oral dosage unit which is then administered from 2-4 times daily.

The following examples are designed solely to illustrate the preparation and use of the compounds of this invention. The temperatures are Centigrade. Other variations of these examples will be obvious to those skilled in the art.

EXAMPLE 1

4-Hydroxyphenylacetic acid (50 g, 0.32 m) in 300 ml of glacial acetic acid was cooled to 10°, at which temperature 100 ml of nitric acid was slowly added. The mixture was allowed to reach room temperature, then was poured into 1 l of water. The separated solid was washed with water and recrystallized from ethanol to give 35 g of 4-hydroxy-3-nitrophenyl acetic acid, m.p. 144°-146°.

A mixture of the nitro compound and 100 ml of thionyl chloride was heated at reflux for 3.5 hours, stripped with toluene twice to leave a solid yellow acid chloride. This was dissolved in chloroform and added dropwise to 109 ml of di-n-propylamine in 200 ml of methylene chloride. The solution was washed with 10% hydrochloric acid and water. The dried solution was stripped. The residue was recrystallized from aqueous methanol, then cyclohexane to give 30 g of N,N-n-propyl-3-nitro-4-hydroxyphenylacetamide, m.p. 63°-65°.

The amide (28 g, 0.1 m) was mixed with 80 ml of water/dimethylformamide, then 36 g (0.26 m) of potassium carbonate. The red mixture was maintained at 35° while 15 ml (0.16 m) of methyl sulfate was added dropwise with stirring. The reaction mixture was quenched in 250 ml of water and extracted with ethyl acetate. The extract was washed with alkali, water, acid and brine. After drying and stripping, the methyl ether product remained.

A mixture of 14.7 g (0.05 m) of this compound and 100 ml of tetrahydrofuran was stirred while 100 ml (0.1 m) of 1.0M boron hydride in tetrahydrofuran was added. The mixture was heated at reflux for 2 hours. 10% Hydrochloric acid (100 ml) was added. Refluxing was continued for 1 hour. The mixture was stripped and 100 ml of 10% hydrochloric acid added. The product was extracted into methylene chloride which was dried and stripped. The residue was placed under low pressure for 2 hours to give 16 g of a yellow oil; N,N-di-n-propyl-3-nitro-4-methoxyphenethylamine hydrochloride.

The tertiary amine (16 g, 0.05 m) was taken up in 250 ml of ethanol and hydrogenated with 0.1 g of platinum oxide at low pressure for 9 hours. The filtered reaction mixture was stripped to give 12.7 g of crude N,N-di-n-propyl-3-amino-4-methoxyphenethylamine hydrochloride which is a key intermediate. After recrystallization from isopropanol/ether, 7.5 g of white diamine, m.p. 139°-141°, was recovered.

The diamine (8.58 g ), in 2 ml of sulfuric acid in 165 ml of water, was mixed with 5.13 g of chloral hydrate, 15.45 g of hydroxylamine sulfate and 42 ml of water. The mixture was heated at reflux briefly, then cooled. After taking the pH to 8 with sodium bicarbonate, the reaction mixture was extracted with chloroform and worked up to give 9.55 g of the desired oxime, m.p. 167°-73°. A second crop melted at 189°-93° (dec.).

The oxime (9.55 g, 0.026 m) was added to 75 ml of sulfuric acid which had been heated to 80°. After addition, the mixture was heated for 15 minutes, then poured onto 300 g of ice. The quenched mixture was taken to pH 8 with bicarbonate and extracted with chloroform. The extracts were washed with water, dried and stripped. The residue was taken into 600 ml of ether, then, treated with ethereal hydrogen chloride to separate 4 g (20%) of 4-[-(2-di-n-propylamino)ethyl]-7-methoxyisatin hydrochloride. Purification over a silica column using (80:19:1) ethyl acetate/methanol/ammonium hydroxide gave the end product and an ether-insoluble by-product.

The 7-methoxy compound (0.5 g, 0.00174 m) was stirred in 2 ml of 48% hydrogen bromide at 115°-120° for 7 hours. Cooling gave a crystalline precipitate which was separated, washed with water and dried to give 350 mg of red crystals; 4-[2-(di-n-propylamino)ethyl]-7-hydroxyisatin hydrobromide, m.p. 257°-8° (dec.).

Anal. Calcd. for $C_{16}H_{23}BrN_2O_3 \cdot H_2O$: C, 49.35; H, 6.42; N, 7.19. Found: C, 49.24; H, 6.04; N, 7.16.

Infrared, nuclear magnetic resonance, and thin layer chromatography data supported the analysis.

A 50 mg portion of the isatin is reacted in ether/carbonate to give the base which is isolated by evaporating the organic extract.

The isatin hydrobromide salt (100 mg) is dissolved in dimethylformamide-pyridine and reacted with a slight excess of isobutyryl chloride to give the 7-O-isobutyryl derivative as the base. Other O-alkanoyl derivatives are prepared in the same manner.

EXAMPLE 2

A mixture of 17.5 g of 3-nitro-4-hydroxyphenylacetic acid and 50 ml of thionyl chloride is heated at refluxe for 5 hours, stripped and azeotroped with toluene to give the acid chloride. A solution of 18.3 g of N-n-propyl-N-(4-methoxyphenethyl)amine in 100 ml of methylene chloride is added with 5 ml of pyridine. The mixture is allowed to stand for 12 hours, then acid washed, dried and stripped to give N-n-propyl-N-(4-methoxyphenethyl)-3-nitro-4-hydroxyphenylacetamide. O-Methylation of 12 g of this compound with carbonate methyl sulfate gives the 4-methoxy-amide. The next two-step reaction, which is carried out as described in Example 1, gives N-n-propyl-N-(4'-methoxyphenethyl)-3-amino-4-methoxyphenethylamine.

This compound (9 g) is reacted with an excess of chloral hydrate and hydroxylamine sulfate in aqueous methanol to give the oxime which is cyclized with sulfuric acid to give 4-[2-(n-propyl-4'-methoxyphenethylamino)-ethyl]-7-methoxyisatin hydrochloride, a product of this invention.

A mixture of 6 g of the dimethoxy compound and 100 ml of methylene chloride is treated with an excess of boron tribromide in methylene chloride at −5°. The mixture was worked up to give 4-[2-(n-propyl-4'-hydrophenethylamino)ethyl]-7-hydroxyisatin hydrobromide.

A 500 mg of aliquot of the salt is shaken with a methylene chloride-5% aqueous sodium bicarbonate mixture. The organic layer is separated, dried and evaporated to give the free base. The base (100 mg) in ether is treated with an excess of methanesulfonic acid to give the methanesulfonic acid salt.

EXAMPLE 3

Using the reaction sequence of Example 1 but substituting the following amines for di-n-propylamine gives the named products:

n-butyl-n-propyamine gives 4-[2-(n-butyl-n-propylamino)etyl]-7-hydroxyisatin hydrochloride;

dimethylamine gives 4-(2-dimethylaminoethyl)-7-hydroxyisatin hydrobromide;

diphenethylamine gives 4-(2-diphenethylaminoethyl)-7-hydroxysatin hydrobromide;

phenethyl-n-propylamine give 4-[2-(phenethyl-n-propylamino)ethyl]-7-hydroxyisatin as the base.

EXAMPLE 4

4-[2-(di-n-propylamino)ethyl]-7-hydroxyisatin hydrobromide (50 mg) is mixed with 200 mg of lactose and 2 mg of magnesium stearate, filled into a hard gelatin capsule with is administered orally to a hypertensive human patient from 1-4 times daily.

What is claimed is:

1. 4-[2-(Di-n-propylamino)ethyl]-7-isobutyryloxyisatin as the free base.

2. 4-[2-(n-Propyl-4'-hydroxypehenethylamino)ethyl]-7-hydroxyisatin or a pharmaceutically acceptable acid addition salt thereof.

* * * * *